(12) United States Patent
Olivan Bescos et al.

(10) Patent No.: US 10,806,520 B2
(45) Date of Patent: Oct. 20, 2020

(54) IMAGING APPARATUS FOR IMAGING A FIRST OBJECT WITHIN A SECOND OBJECT

(71) Applicant: KONINKLIJKE PHILIPS N.V., Eindhoven (NL)

(72) Inventors: Javier Olivan Bescos, Eindhoven (NL); Thijs Elenbaas, Nijmegen (NL); Marco Verstege, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 809 days.

(21) Appl. No.: 15/306,790

(22) PCT Filed: May 13, 2015

(86) PCT No.: PCT/EP2015/060559
§ 371 (c)(1),
(2) Date: Oct. 26, 2016

(87) PCT Pub. No.: WO2015/177012
PCT Pub. Date: Nov. 26, 2015

(65) Prior Publication Data
US 2017/0095296 A1    Apr. 6, 2017

(30) Foreign Application Priority Data

May 23, 2014  (EP) .................................... 14169585

(51) Int. Cl.
*A61B 34/20* (2016.01)
*A61B 17/00* (2006.01)
(Continued)

(52) U.S. Cl.
CPC .... *A61B 34/20* (2016.02); *A61B 2017/00778* (2013.01); *A61B 2034/107* (2016.02);
(Continued)

(58) Field of Classification Search
CPC ... A61B 34/20; A61B 34/2051; A61B 8/4245; A61B 17/3478; A61B 2017/00252; A61B 2034/2051; A61B 2034/107
See application file for complete search history.

(56) References Cited

U.S. PATENT DOCUMENTS 6,336,899 B1 * 1/2002 Yamazaki ............ A61B 8/0833
                                                             128/916
6,912,471 B2   6/2005 Heigl et al.
(Continued)

OTHER PUBLICATIONS

Manstad-Hulaas, F. et al., "Three-dimensional electromagnetic navigation vs. fluoroscopy for endovascular aneurysm repair: a prospective feasibility study in patients", J. Endovasc ther. Feb. 2012; 19(1):70-8. Abstract.

*Primary Examiner* — Elmer M Chao

(57) ABSTRACT

An imaging apparatus images a first object (10), like a tip of a catheter, disposed within a second object, such as a vascular structure of a person. A three-dimensional representation of the second object including a representation of a surface (23) of the second object and the position of the first object relative to the position of the second object are provided. A projection (22) of the first object onto the representation of the surface of the second object is determined and shown to a user like a physician on a display (18). The three-dimensional spatial relationship between the first object and the second object is thereby shown in a way that is very native for the user, i.e. a visualization can be provided, which allows the user to easily and accurately grasp the three-dimensional spatial relationship between the first object and the second object.

15 Claims, 7 Drawing Sheets

(51) Int. Cl.
*A61B 90/00* (2016.01)
*A61B 34/10* (2016.01)

(52) U.S. Cl.
CPC .............. *A61B 2034/2051* (2016.02); *A61B 2034/2065* (2016.02); *A61B 2090/364* (2016.02); *A61B 2090/367* (2016.02); *A61B 2090/3764* (2016.02)

(56) References Cited

U.S. PATENT DOCUMENTS

| | | |
|---|---|---|
| 8,320,711 B2 | 11/2012 | Altmann et al. |
| 8,467,855 B2 | 6/2013 | Yasui |
| 8,600,138 B2 | 12/2013 | Gorges et al. |
| 8,632,468 B2 | 1/2014 | Glossop et al. |
| 8,831,307 B2 | 9/2014 | Cagnan et al. |
| 2004/0210403 A1 | 10/2004 | Heigl et al. |
| 2007/0286336 A1 | 12/2007 | Bernard et al. |
| 2008/0033285 A1 | 2/2008 | Camus et al. |
| 2009/0069672 A1 | 3/2009 | Pfister et al. |
| 2009/0281418 A1 | 11/2009 | Ruijters et al. |
| 2010/0020161 A1 | 1/2010 | Bertrams et al. |
| 2010/0217117 A1 | 8/2010 | Glossop et al. |
| 2013/0172906 A1 | 7/2013 | Olson et al. |
| 2013/0218024 A1 | 8/2013 | Boctor et al. |
| 2013/0336558 A1 | 12/2013 | Manzke et al. |
| 2014/0031665 A1 | 1/2014 | Pinto et al. |

\* cited by examiner

IMAGING APPARATUS FOR IMAGING A FIRST OBJECT WITHIN A SECOND OBJECT

CROSS-REFERENCE TO PRIOR APPLICATIONS

This application is the U.S. National Phase application under 35 U.S.C. § 371 of International Application Serial No. PCT/EP2015/060559, filed on May 13, 2015, which claims the benefit of European Patent Application No. 14169585.8, filed on May 23, 2014. These applications are hereby incorporated by reference herein.

FIELD OF THE INVENTION

The invention relates to an imaging apparatus, an imaging method and an imaging computer program for imaging a first object like a tip of a catheter within a second object like a vascular structure of a living being. The invention relates further to a system for moving the first object within the second object, which comprises the imaging apparatus.

BACKGROUND OF THE INVENTION

US 2010/0217117 A1 discloses a system for performing an image-guided transvascular shunting procedure between a first vessel and a target vessel in a portion of an anatomy of a patient, wherein the system is adapted to produce, based on positional orientation information about a puncture needle tip and a path of a target vessel, a display of a position of the puncture needle relative to the target vessel and an extended path of the puncture needle, wherein the extended path includes a path which the puncture needle will follow, if the puncture needle is extended past a distal end portion of a guide needle. The display further shows a point at which the puncture needle will intersect the target vessel, if the extended path of the puncture needle intersects the determined path of the target vessel, and an indicator of the closest approach from the puncture needle to the target vessel, if the extended path of the puncture needle does not intersect the path of the target vessel.

In catheterization procedures it is important to know the position of a catheter within an inner structure of a person, through which the catheter should be navigated. For this reason generally a real-time x-ray projection image is generated during the catheterization procedure, wherein a physician moves the catheter within the inner structure based on the generated x-ray projection image. However, since the x-ray projection image is a two-dimensional image only, it is difficult for the physician to accurately grasp the three-dimensional position of the catheter within the inner structure and hence to accurately navigate the catheter tip within the inner structure.

SUMMARY OF THE INVENTION

It is an object of the present invention to provide an imaging apparatus, method and computer program for imaging a first object within a second object, which allows a user to more accurately move the first object within the second object. It is a further object of the present invention to provide a moving system for moving the first object within the second object, which comprises the imaging apparatus.

In a first aspect of the present invention an imaging apparatus for imaging a first object within a second object is presented, wherein the imaging apparatus comprises:

- a representation providing unit for providing a three-dimensional representation of the second object, wherein the three-dimensional representation includes a representation of a surface of the second object,
- a position providing unit for providing the position of the first object relative to position of the second object,
- a projection unit for determining a projection of the first object onto the representation of the surface of the second object based on the provided position of the first object, and
- a display for displaying the projection of the first object on the representation of the surface of the second object.

Since the projection unit determines a projection of the first object onto the representation of the surface of the second object based on the provided position of the first object relative to the position of the second object and thus relative to the representation of the surface of the second object, wherein the projection of the first object on the representation of the surface of the second object depends on the three-dimensional spatial relationship between the position of the first object and the surface of the second object and illustrates this three-dimensional spatial relationship in a way that is very native for a user like a physician, a visualization can be provided, which allows the user to easily and accurately grasp the three-dimensional spatial relationship between the first object and the second object and hence to more accurately move the first object within the second object.

The first object is preferentially a tip of an interventional device like the tip of a catheter or a needle to be introduced into a living being, and the second object is preferentially a vascular structure or another part of the living being, wherein the interventional device should be navigated within the vascular structure.

The representation providing unit is preferentially adapted to provide a three-dimensional image of the second object as the representation. The image may be computed tomography image, a magnetic resonance image, an ultrasound image or a three-dimensional image of another imaging modality. The representation providing unit can also be adapted to provide a three-dimensional model of the second object as the representation. For instance, the representation providing unit can be adapted to provide a polygon mesh representing the second object as the representation. Moreover, the representation providing unit can also be adapted to provide an implicit surface as the representation of the surface of the second object.

The representation providing unit may be a storing unit, in which the three-dimensional representation of the second object is stored already and from which the stored three-dimensional representation can be retrieved for providing the same. The representation providing unit can also be a receiving unit for receiving the three-dimensional representation of the second object and for providing the received three-dimensional representation. Moreover, the representation providing unit can be adapted to generate the three-dimensional representation of the second object. For instance, the representation providing unit can be an imaging modality for generating a three-dimensional image of the second object, wherein the generated three-dimensional image may be regarded as being the three-dimensional representation. The imaging modality can be, for instance, a magnetic resonance imaging modality, a computed tomography imaging modality, a nuclear imaging modality like a positron emission tomography or a single photon emission tomography imaging modality, an ultrasound imaging modality, et cetera. The representation providing unit can also be adapted to determine a model of the second object as the three-dimensional representation based on a provided three-dimensional image. For example, at least the surface of the second object, onto which the first object should be projected, can be segmented in the provided three-dimensional image, in order to determine the representation of the surface of the second object.

Also the position providing unit can be a storing unit, wherein in this case the position providing unit is adapted to store the position of the first object relative to the position of the second object and to retrieve the stored position for providing the same. The position providing unit can also be adapted to receive the position of the first object from a position determination device and to provide the received position. The position providing unit can also be a position determination device, which is adapted to determine the position of the first object relative to the position of the second object and to provide the determined position. In particular, the position providing unit is adapted to provide the position of the first object relative to the position of the second object by using optical shape sensing and/or by using electromagnetic sensors and/or by using x-rays. For instance, the position providing unit can be adapted to acquire x-ray projection images of the first object within the second object in at least two different acquisition directions, wherein the first object can be identified in the x-ray projection images and the position of the first object relative to the second object can be determined based on the position of the identified first object within the x-ray projection images under consideration of the respective acquisition directions. The determination of the position of the first object is preferentially registered with the representation of the second object, in order to provide the position of the first object relative to the position of the second object. For instance, the x-ray projection images, which may be used for determining the position of the first object, can be registered with the representation of the second object, in order to register the determined position of the first object with the representation of the second object position. Or, if optical shape sensing and/or electromagnetic sensing are used for determining the position of the first object relative to the second object, an optical shape sensing system and/or an electromagnetic sensing system can be registered with the representation of the second object, in order to determine the position of the first object relative to the position of the second object.

In an embodiment the position providing unit is adapted to also provide the orientation of the first object relative to the second object, wherein the projection unit is adapted to calculate the projection of the first object onto the representation of the surface of the second object based on the provided position and orientation of the first object. For instance, if the first object is a tip of an interventional device, the position of the tip may be defined as being the most distal position of the center point at the tip of the interventional device, wherein the tip may be longish, i.e. extended along a longitudinal axis, and wherein the orientation of the tip may be defined as being the orientation of the longitudinal axis of the tip. The projection unit may be adapted to calculate the projection based on the point of intersection between the representation of the surface of the second object and a line defined by the position and orientation of the first object. In particular, the projection unit may be adapted to calculate the projection such that the point of intersection forms the center of the projection. Considering also the orientation of the first object relative to the second object further improves the three-dimensional impression which can be provided to the user moving the first object within the second object.

The projection is a two-dimensional projection onto the representation of the surface of the second object. The two-dimensional projection depends on the three-dimensional spatial relationship between the first object and the second object, especially on the distance between the first object and the second object and/or the orientation of the first object relative to the second object.

In a further embodiment the projection unit is adapted to a) calculate for different surface positions on the representation of the surface of the second object a projection value that depends on the distance between the respective surface position and a further position that depends on the provided position of the first object, b) provide assignments between projection values and visualization properties, and c) assign visualization properties to the surface positions based on the calculated projection values and the provided assignments, thereby determining the projection. The projection unit may be adapted to calculate a distance between the provided position of the first object and the respective surface position as the projection value, or to calculate a point of intersection between the representation of the surface of the second object and a line defined by the position and orientation of the first object and to calculate a distance between the point of intersection and the respective surface position as the projection value. The distance between the point of intersection and the respective surface position is preferentially calculated along the representation of the surface of the second object. Moreover, the calculated distances are preferentially the respective minimal distances, and the visualization properties are preferentially degrees of opacity and/or colors and/or brightness. These techniques for determining the projection of the first object on the representation of the surface of the second object can further improve the three-dimensional impression provided to the user, which can lead to an even more accurate movement of the first object within the second object.

It is preferred that the display is further adapted to display a representation of the position of the first object relative to the representation of the surface of the second object. Moreover, the imaging apparatus may further comprise an image providing unit for providing an image of the first object, wherein the display may be adapted to display the projection of the first object on the representation of the surface overlaid with the provided image. Preferentially, the provided image shows the first object within the second object, i.e. the provided image preferentially shows the second object and the first object within the second object. The image providing unit may be a storing unit for storing the image of the first object and for retrieving the stored image for providing the same. The image providing unit can also be a receiving unit for receiving the image from an imaging modality and for providing the received image. Furthermore, the image providing unit can be adapted to generate the image of the first object, preferentially after the first object has been introduced into the second object, and to provide the generated image. The image is preferentially a live image showing the second object and the first object within the second object. It is, for instance, an x-ray projection image which is generated by an x-ray projection system like an x-ray C-arm system. By overlaying the provided image of the first object on the visualization of the projection of the first object on the representation of the surface of the second object and/or by displaying the representation of the position of the first object relative to the representation of the surface of the second object, on which already the projection is shown, the three-dimensional information, which a user may grasp from the resulting features shown on the display, may allow the user to further improve the accuracy of moving the first object within the second object.

The display is preferentially adapted such that the projection of the first object on the representation of the surface of the second object is viewable by a user in a viewing direction. In an embodiment the second object comprises a wall having a front surface with respect to the viewing direction at one side of the wall and a back surface with respect to the viewing direction at another opposing side of the wall, wherein the projection unit is adapted to assign a visualization property to the determined projection depending on whether the representation of the surface of the second object, on which the projection has been determined, represents the front surface or the back surface of the second object, and wherein the display is adapted to display the projection of the first object depending on the assigned visualization property. The different visualization properties for the front and back surfaces can be, for instance, solid lines/dashed lines and/or different colors and/or different degrees of opacity and/or different brightnesses et cetera.

The projection unit can be adapted to provide assignments between a) whether the surface, on which the projection is determined, is a front surface or a back surface and b) visualization properties and to use these assignments for assigning a visualization property to the determined projection. The assignments can be predetermined assignments which may be modifiable by a user via a user interface.

The second object can comprise a wall having one first surface and one opposing second surface, wherein the three-dimensional representation can include a representation of one or several of the first and second surfaces. Generally, the representation will represent one first surface and one second surface. However, in case of noise in an image which may be used for providing the representation, the representation can represent several first surfaces and/or several second surfaces. The projection unit can be adapted to determine which surface is a front surface and which surface is a back surface with respect to the viewing direction by using known techniques. For instance, if it can be assumed that a surface is non-planar, a normal vector of the surface can be determined, wherein it can be defined that the normal vector is outward pointing with respect to the curvature of the surface and wherein it can be determined whether the surface is a front surface or a back surface based on the normal vector and the viewing direction. In particular, it can be determined whether a surface is the front surface or the back surface based on the sign of the scalar product of the normal vector and a vector representing the viewing direction.

If the representation represents several surfaces of the second object on which the first object could be projected, the projection unit can comprise selection rules for selecting a surface on which the projection should be determined. For instance, the selection rules can define that the projection should be determined on the surface having the shortest distance to the first object, or they can define that the projection should be determined on the surface having the longest distance to the first object. Moreover, the selection rules may define that the projection should be determined on the first one of the several surfaces with respect to the viewing direction or the selection rules may define that the projection should be determined on the last one of the several surfaces with respect to the viewing direction, i.e. that the projection should be determined on the surface having the longest distance to the assumed viewer used for displaying the projection or on the surface having the shortest distance to the viewer.

It is further preferred that the imaging apparatus comprises a target providing unit for providing a representation of a target within the second object to which the first object should be moved, wherein the display is adapted to also display the representation of the target. Also showing a representation of the target on the display, to which the first object should be moved within the second object, can improve the accuracy of moving the first object within the second object.

In a further aspect of the present invention a system for moving a first object within a second object is presented, wherein the system comprises:
 a moving unit for moving the first object within the second object, and
 an imaging apparatus as defined in claim 1 for imaging the first object within the second object.

The system is preferentially adapted to move an interventional device like a catheter within a vascular structure of the person or an animal. The moving unit is preferentially adapted to allow a user like a physician to manually move the first object within the second object. For instance, the moving unit can comprise guidewires, steering wires, et cetera for allowing the user to move the first object within the second object. The moving unit can also comprise robotic means which can allow the user to move the first object within the second object by using, for instance, a joystick or another input unit for inputting steering commands into the robotic system.

In another aspect of the present invention an imaging method for imaging a first object within a second object is presented, wherein the imaging method comprises:
 providing a three-dimensional representation of the second object, wherein the three-dimensional representation includes a representation of a surface of the second object, by a representation providing unit,
 providing the position of the first object relative to the second object by a position providing unit,
 determining a projection of the first object onto the representation of the surface of the second object based on the provided position of the first object by a projection unit, and
 displaying the projection of the first object on the representation of the surface of the second object by a display.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
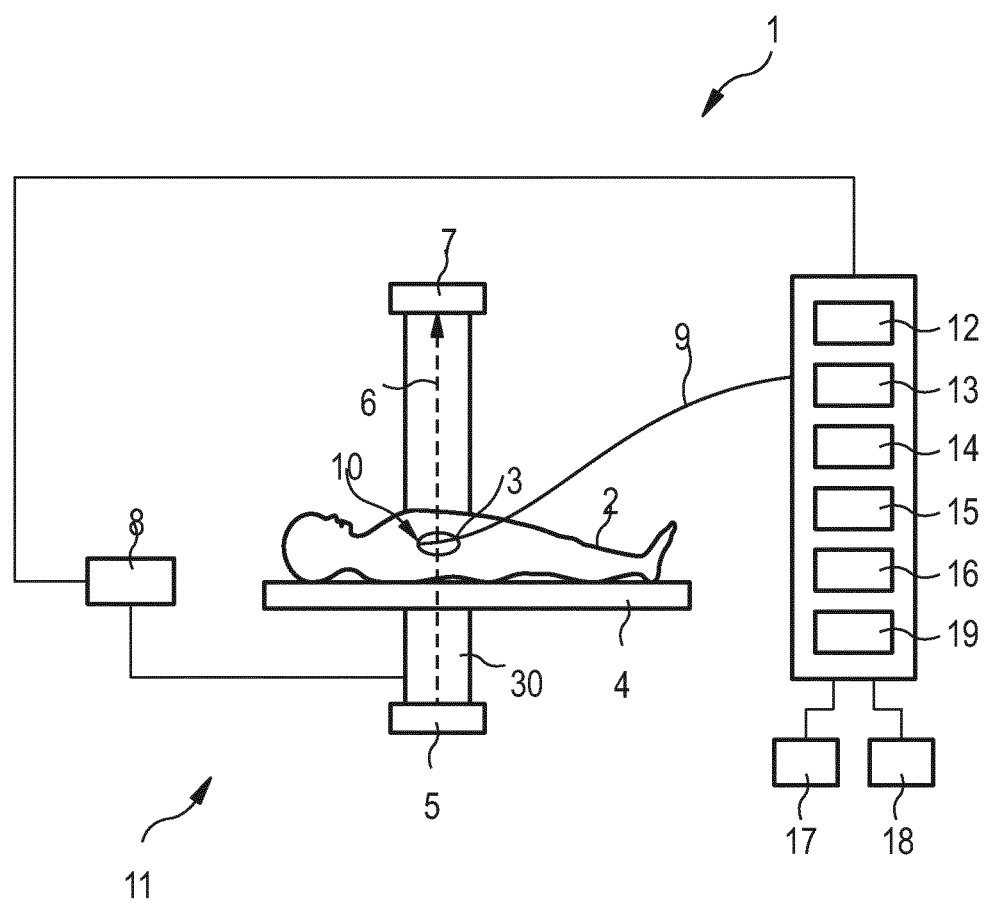
FIG. 1 shows schematically and exemplarily an embodiment of a system for moving a tip of a catheter within a vascular structure.

FIG. 1 shows schematically and exemplarily a system for moving a first object within a second object. In this embodiment the system is an interventional system 1 for moving a catheter 9 with a tip 10 being the first object within a vascular structure 3 in a person 2 lying on a support means 4 like a table, in order to perform an interventional procedure. The vascular structure 3 within the person 2 is the second object in this embodiment.

The system comprises a representation providing unit 12 for providing a three-dimensional representation of the vascular structure 3, wherein the three-dimensional representation includes a representation of a surface of the vascular structure 3. In this embodiment the three-dimensional representation is formed by a segmentation of the vascular structure 3 in a pre-interventional image like a pre-interventional computed tomography or magnetic resonance image. The system further comprises a position providing unit 13 for providing the position and orientation of the tip 10 of the catheter 9 within the vascular structure 3. In this embodiment the catheter 9 comprises an optical shape sensing fiber and the position providing unit 13 is an optical shape sensing control and determination unit, in order to determine the position and orientation of the tip 10 of the catheter 9 by optical shape sensing. In other embodiments the position providing unit can be adapted to determine the position of the tip 10 of the catheter 9 by other means like electromagnetic means.

Figure 2:
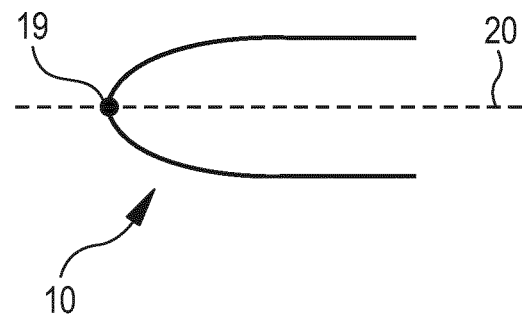
FIG. 2 shows schematically and exemplarily a most distal point of the tip of the catheter and a longitudinal axis of the tip of the catheter.
Figure 3:
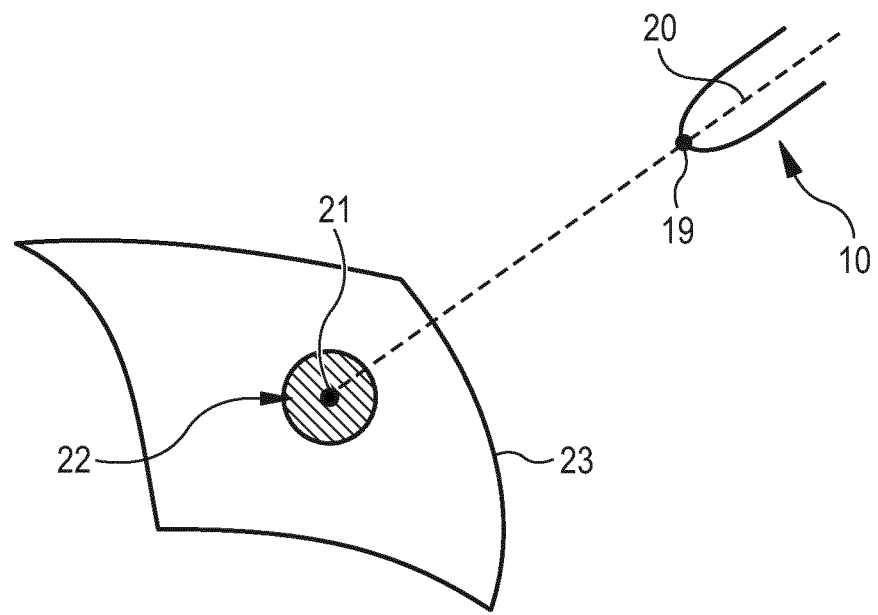
FIG. 3 illustrates schematically and exemplarily a projection of the tip of the catheter on a surface of the vascular structure.

The system further comprises a projection unit 14 for determining a projection of the tip of the catheter 10 onto the representation of the surface of the vascular structure 3 based on the provided position and orientation of the tip 10 of the catheter 9. The tip 10 of the catheter 9 is schematically and exemplarily illustrated in FIG. 2, wherein in FIG. 2 the most distal point 19 at the center of the distal end of the tip 10 and the longitudinal axis 20 of the tip 10 are shown. The position providing unit 13 is preferentially adapted to provide the position of this most distal point 19 as the position of the tip 10 of the catheter 9 and the orientation of the longitudinal axis 20 as the orientation of the tip 10 of the catheter 9. The projection unit 14 is preferentially adapted to calculate the point of intersection 21 between the representation of the surface 23 of the vascular structure 3 and a line defined by the position of the most distal point 19 of the tip 10 and the orientation of the longitudinal axis 20 of the tip 10 as schematically and exemplarily illustrated in FIG. 3. If the surface encloses the tip 10 of the catheter as it is generally the case if the catheter is moved within a vessel, the intersection point is calculated in the direction in which the tip of the catheter points, i.e. in the direction pointing from the tip body to the most distal point 19 of the tip.

The projection unit 14 is preferentially further adapted to determine the projection 22 of the tip 10 of the catheter 9 on the representation of the surface 23 such that the projection 22 is centered on the determined point of intersection 21. Moreover, the projection unit 14 is preferentially further adapted to calculate for different surface positions on the representation of the surface 23 of the vascular structure 3 projection values being indicative of the distance between the respective surface position and a further position that depends on the provided position of the tip 10 of the catheter 9. This determination of the projection values is preferentially restricted to a predefined area around the point of intersection 21. For instance, the projection values may only be determined within a predefined region around the intersection point 21 covering only surface positions having a distance to the point of intersection 21 being smaller than a predefined threshold.

In particular, the projection unit 14 is adapted to calculate a distance between the point of intersection 21 and the respective surface position along the representation of the surface 23 of the vascular structure 3 or the distance between the provided position of the most distal point 19 of the tip 10 of the catheter 9 and the respective surface position as the projection value. The calculated distances correspond preferentially to the respective smallest distance, i.e. to the length of the smallest path between the two respective locations.

The projection unit 14 is further adapted to provide assignments between projection values and visualization properties. The visualization properties define preferentially degrees of opacity and/or colors and/or brightness. The assignments may be provided as transfer functions transferring a respective projection value to one or several visualization properties. The projection unit 14 is further adapted to assign the visualization properties to the surface positions based on the calculated projection values and the provided assignments, in order to determine the projection 22. The system further comprises a display 18 for displaying the projection 22 of the tip 10 of the catheter 9 on the representation of the surface 23 of the vascular structure 3. The display 18 may be further adapted to display a representation of the position of the tip 10 of the catheter 9 relative to the representation of the inner surface 23 of the inner structure 3.

The system further comprises an image providing unit 11 being, in this embodiment, a fluoroscopy device for imaging the tip 10 of the catheter 9 within the vascular structure 3 during the interventional procedure. The fluoroscopy device 11 comprises an x-ray source 5 for emitting x-rays 6 traversing the person 2 lying on the support means 4. The fluoroscopy device 11 further comprises an x-ray detector 7 for detecting the x-rays 6, after having traversed the person 2. The x-ray source 5 and the x-ray detector 7 are mounted on a C-arm 30, which is rotatable with respect to the person 2, in order to irradiate the person 2 in different directions. Moreover, the support means 4 and the C-arm 30 may be translatable with respect to each other, in order to irradiate different parts of the person 2. The x-ray detector 7 is adapted to generate detection signals being indicative of the detected x-rays 6, wherein the detection signals are transmitted to a fluoroscopy control unit 8, which is adapted to control the C-arm 30, the x-ray source 5 and the x-ray detector 7 and to generate two-dimensional projection images depending on the received detection signals. The display 18 can be adapted to display the calculated projection of the tip 10 of the catheter 9 on the representation of the surface 23 overlaid with the x-ray projection image generated by the fluoroscopy device 11, in order to allow the user to accurately monitor the position of the tip 10 of the catheter 9 within the vascular structure 3 during the interventional procedure. The display 18 can be adapted to perform a 2D-3D registration, in order to register the two-dimensional x-ray projection image with the three-dimensional representation of the vascular structure and to accurately overlay them onto each other.

The fluoroscopy device 11 can also be adapted to be used for registering the position providing unit 13 with the three-dimensional representation. For instance, in a calibration step the position and shape of the catheter 9 can be determined by optical shape sensing, while the catheter 9 has a known shape and is in a known position and orientation relative to the fluoroscopy device 11, in order to register the position providing unit 13 relative to the fluoroscopy device 11. During the calibration process the shape, position and orientation of the catheter 9 relative to the fluoroscopy device 11 may be a priori known or it may be determined based on several x-ray projection images, which have been acquired in different acquisition directions by the fluoroscopy device 11 and which show the catheter 9. Since in addition the x-ray projection image provided by the fluoroscopy device 11 can be registered with the three-dimensional representation, for example, by performing a 2D-3D registration, the three-dimensional representation can be registered with the position and orientation of the tip 10 of the catheter 9 determined by the position providing unit 13. In other embodiments the different systems can be registered to each other by using other known registration techniques.

The system further comprises a target providing unit 19 for providing a representation of a target within the vascular structure 3 to which the tip 10 of the catheter 9 should be moved, wherein the display 18 is preferentially adapted to also display this representation of the target. The target providing unit 19 can be adapted to provide an already stored representation of the target, which just needs to be retrieved for providing the same to the display 18 which shows the representation of the target. However, the target providing unit 19 can also be adapted to provide a graphical user interface allowing the user to completely manually or semi-automatically indicate the target in the three-dimensional representation of the vascular structure 3, wherein then the marker can be used as a representation of the target shown by the display 18. The target providing unit 19 can also be adapted to automatically determine a target based on the provided three-dimensional representation of the vascular structure 3. For instance, the target providing unit 19 can be adapted to automatically identify a certain branch between a certain artery and a main artery of the vascular structure 3 like the position where the renal artery branches from the main artery.

Since the representation providing unit 12, the position providing unit 13, the projection unit 14, the display 18, the image providing unit 11 and the target providing unit 19 all contribute to the final displaying of the projection of the tip of the catheter on the representation of the surface of the vascular structure, wherein this displaying can also involve displaying the representation of the target, the image provided by the fluoroscopy device 11 and/or a representation of the tip 10 of the catheter 9, these components can be regarded as being components of an imaging apparatus for imaging the first object within the second object, i.e. for imaging the tip of the catheter within the vascular structure.

The system 1 further comprises a catheter control unit 15 for controlling the catheter, for instance, for energizing the tip of the catheter for performing an ablation procedure, for actuating the tip of the catheter for inserting a stent graft, for sensing a property of the wall of the vascular structure like an electrical property, et cetera. Moreover, the system comprises a navigation unit or moving unit 16 for navigating the tip 10 of the catheter 9 within the vascular structure 3, wherein the navigation unit 16 can use steering wires, robotic means, et cetera for allowing a user to navigate and move the tip 10 of the catheter 9 within the vascular structure 3. The system further comprises an input unit 17 like a keyboard, a computer mouse, a touchpad, et cetera, in order to allow the user to input commands into the system 1 like commands for controlling the catheter control unit 15, commands for controlling the navigation unit 16, commands for controlling the fluoroscopy device 11, commands for setting visualization parameters for visualizing the projection of the tip of the catheter on top of the surface of the vascular structure, et cetera.

The representation providing unit 12 can be adapted to provide the three-dimensional representation of the vascular structure 3 such that it includes a representation of a first surface and of an opposing second surface of a wall of the vascular structure 3, wherein the projection unit 14 can be adapted to determine distances a) between the position of the tip 10 of the catheter 9 and the represented first surface of the wall of the vascular structure 3 and b) between the position of the tip 10 of the catheter 9 and the represented second surface of the wall of the vascular structure 3 and to determine, on which surface the projection should be determined, based on the determined distances. The distances are preferentially respective shortest distances. The projection unit 14 can be adapted to determine the projection on the surface for which the smallest distance has been determined. Moreover, the display 18 can be adapted such that the projection of the tip 10 of the catheter 9 on the representation of the surface of the vascular structure 3 is viewable by a user in a viewing direction, wherein the projection unit 14 can be adapted to determine, based on the viewing direction and, for instance, the respective normal vector, which of the first and second surfaces is the front surface and which of the first and second surfaces is the back surface with respect to the viewing direction. In addition, the projection unit 14 can be adapted to assign a visualization property to the determined projection depending on whether the projection has been determined on the front surface or on the back surface, wherein the display 18 can be adapted to display the projection of the tip 10 of the catheter 9 depending on the assigned visualization property. The different visualization properties for the inner and outer surfaces can be, for instance, solid lines/dashed lines and/or different colors and/or different degrees of opacity and/or different brightnesses et cetera. The projection unit 14 can be adapted to provide assignments between a) whether the surface, on which the projection is determined, is the front surface or the back surface and b) visualization properties and to use these assignments for assigning a visualization property to the determined projection. The assignments can be predetermined assignments which may be modifiable by a user via a user interface.

Figure 4:
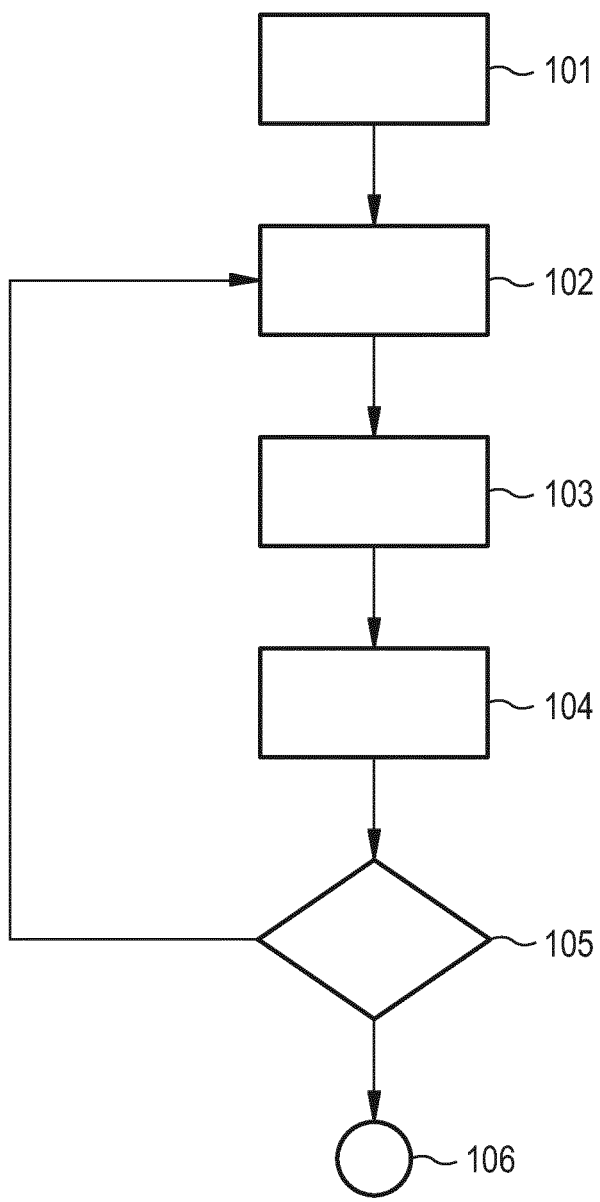
FIG. 4 shows a flowchart exemplarily illustrating an embodiment of an imaging method for imaging the tip of the catheter within the vascular structure.

In the following an embodiment of an imaging method for imaging a first object within a second object will exemplarily be described with reference to a flowchart shown in FIG. 4.

In step 101 a three-dimensional representation of the second object is provided, wherein the three-dimensional representation includes a representation of a surface of the second object. In particular, a three-dimensional representation of a vascular structure within a person is provided in step 101. In step 102 the position of the first object within the second object, especially the position of a tip of a catheter within the vascular structure, is determined by using, for instance, optical shape sensing or an electromagnetic tracking technique. In step 103 a projection of the first object onto the representation of the surface of the second object is determined based on the provided position of the first object, and in step 104 the projection of the first object on the representation of the surface of the second object is displayed. In particular, a projection of the tip of the catheter onto a representation of the surface of the vascular structure is determined and displayed. In step 105 it is determined whether an abort criterion is fulfilled, wherein, if this is not the case, the method continues with step 102 such that the position of the first object is continuously provided, the projection is continuously determined and the determined projection is continuously displayed in a loop, in order to allow a user to monitor the position of the first object within the second object, while the user moves the first object within the second object. If in step 105 the abort criterion is fulfilled, the imaging method ends in step 106. The abort criterion can be, for instance, whether the user has input a stop command indicating that the imaging method should stop.

The imaging method can of course comprise further steps like additionally providing a live image showing the first object within the second object like a fluoroscopy image generated by the fluoroscopy device 11, wherein the provided live image can also be shown on the display 18. Moreover, the display 18 can be adapted to show a representation of the first object at the provided position of the first object relative to the position of the representation of the surface of the second object.

During minimally invasive operations a user like a surgeon may navigate a clinical device like a catheter, a guidewire, stent grafts, et cetera through the vessels of a person. These navigation procedures require the user to be able to visualize or track the clinical devices, while there are advanced through the vessels, which are preferentially blood vessels. In order to visualize or track these clinical devices conventional x-ray imaging, magnetic resonance imaging, computed tomography imaging, et cetera may be used. Moreover, for tracking the clinical devices tracking systems like optical shape sensing or electromagnetic tracking systems can be used. Also a stereoscopic biplane x-ray system could be used, in order to track the clinical devices in three dimensions. Especially for complex surgical procedures such as a fenestrated endovascular aneurysm repair (FE-VAR), a three-dimensional model, i.e. a three-dimensional representation, of the vasculature may be generated prior to the operation. Such a pre-operative or pre-interventional three-dimensional model may be overlaid on top of live images acquired during the operation. For instance, a three-dimensional model of vessels may be overlaid on top of a live two-dimensional x-ray projection image, wherein in addition to some anatomic structures such as, for instance, the spine different clinical, in this case endovascular, devices may be observed in the two-dimensional x-ray projection image such as a guidewire and a catheter.

A very important step during minimally invasive procedures such as FEVAR, EVAR, vascular embolization, et cetera is the introduction of a catheter inside a side branch of a main vessel. For instance, during such a procedure a physician may want to insert a catheter tip into the renal artery. In known systems the physician uses a two-dimensional x-ray projection image, in order to navigate the catheter within the three-dimensional vascular structure. In this case the depth information of the exact location of the catheter tip is missing, making the task of inserting the catheter into the renal artery very cumbersome. This can be compared with the task of trying to insert a thread inside an opening of a sewing needle when only one eye is opened, thereby missing the depth information. In order to overcome the problems derived from the two-dimensional nature of the x-ray projection image, the imaging apparatus and imaging method described above with reference to FIGS. 1 to 4 display a calculated projection of the catheter tip on top of a three-dimensional representation of a vascular structure. The depth perception is preferentially enhanced by, for instance, casting a shadow or a shining spot on a vessel wall, i.e. on a wall of the vascular structure, wherein, in the case of casting a shadow, the projection darkens the vessel wall and, in the case of a shining spot, the projection brightens the vessel wall. The assignments provided by the projection unit 14, i.e. the transfer function, can be configured accordingly. The projection unit 14 may be adapted to calculate the projection on the surface of the vascular structure such that, if the distance between the catheter tip and the inner wall becomes larger, the calculated projection becomes less focused, and, when the distance between the tip of the catheter and the surface becomes smaller, the projection will be more focused. In order to provide a less focused projection, the projection unit can be adapted to provide a wider and/or less intense and/or less blurry projection. Because the visualization emulates a natural phenomenon, the effect is intuitively understood and users are already trained in assessing the direction as well as the distance.

Figure 5:
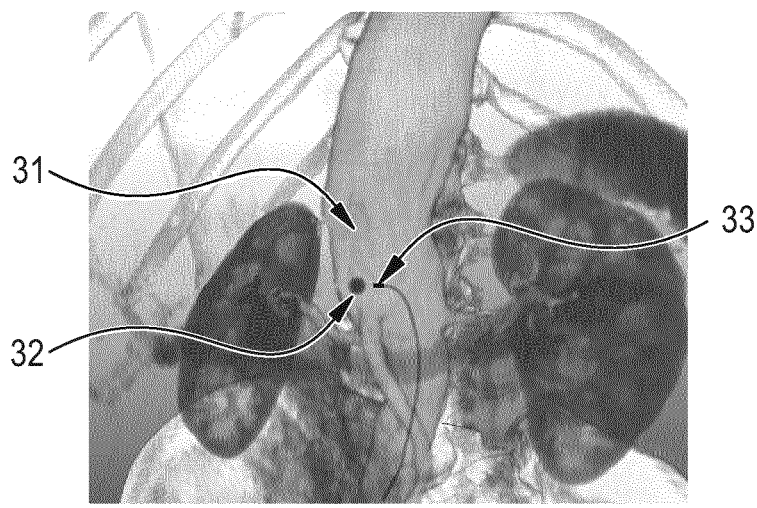
FIGS. 5, 6 and 10 show examples of a projection of the tip of the catheter on a representation of a surface of the vascular structure.
Figure 6:
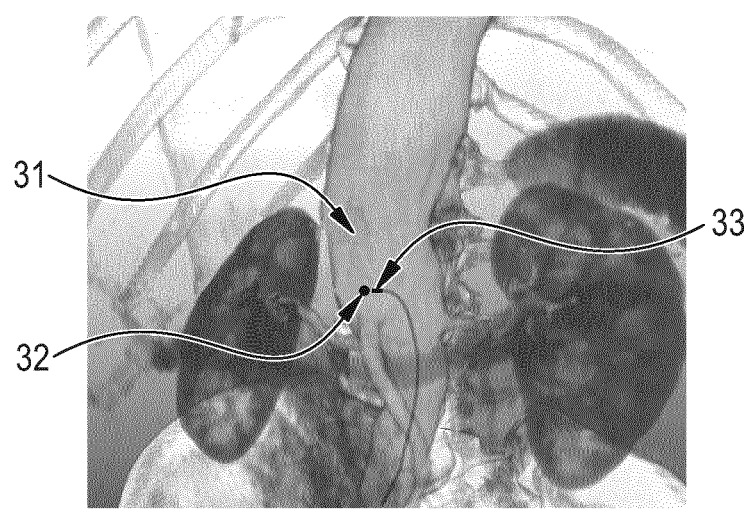

FIG. 5 shows schematically and exemplarily a representation of a vascular structure 31 and a representation of a tip 33 of a catheter. Moreover, FIG. 5 shows a projection 32 of the tip 33 onto a surface of the vascular structure 31. Since in the situation shown in FIG. 5 the distance between the tip of the catheter and the surface of the vascular structure is relatively large, the projection 32 is not well-focused and seems to be a little blurry. FIG. 6 schematically and exemplarily illustrates another situation, in which the tip of the catheter is very close to the inner wall of the vascular structure. The projection 32 of the tip of the catheter onto the surface of the vascular structure is therefore relatively focused, i.e. smaller and sharper than in FIG. 5.

In an embodiment the imaging apparatus and method are adapted to provide three-dimensional data of the vasculature of a person such as a pre-operative computed tomography, magnetic resonance, three-dimensional ultrasound, et cetera imaging data set as a three-dimensional representation. Also a polygon mesh describing the vasculature of the person could be provided as a representation of the vasculature. Moreover, the imaging apparatus and method may be adapted to derive the three-dimensional shape of a navigational medical device like a catheter, i.e. its three-dimensional position and orientation. In particular, the location of the tip and the orientation of the tip may be provided. For deriving this information systems like optical shape sensing or electromagnetic tracking systems may be used. As another option the three-dimensional shape of the medical device may be reconstructed from images acquired during the interventional procedure. For example, a guidewire reconstruction may be performed based on two x-ray projection images acquired by a biplane x-ray system. It is also possible to reconstruct the three-dimensional shape of the medical device from two or more x-ray projection images acquired with a monoplane x-ray system, wherein in this case it is assumed that the medical device does not move during the acquisition of these x-ray projection images.

Moreover, the imaging apparatus and method are adapted to project preferentially the tip of the navigation medical device on top of the three-dimensional vascular data. The position and orientation of the tip of the medical device may be defined by the position of a three-dimensional point P on top of the device, for example, by the three-dimensional position of the most distal center point of the tip of the medical device, and by a three-dimensional vector V indicating the orientation of the tip of the medical device. The projection unit can be adapted to calculate the center of the projection by calculating the intersection between the line defined by (P, V) and the inner surface of the vascular structure derived from the three-dimensional pre-operative data. If C is the intersection point between the line (P, V) and the inner surface of the vascular structure, for each point PS on the inner surface of the vascular structure in a neighborhood of C a distance can be defined like the three-dimensional Euclidean distance between P and PS or like the distance of the minimum length path between C and PS over the inner surface of the vascular structure. The respective distances can be regarded as being projection values determined for the different surface positions in the neighborhood of C. The projection unit can further be adapted to provide a transfer function TF for mapping the projection values, i.e. the respective distances D in this example, to degrees of opacity and colors, which may be described by TF(D) →RGBA. For each point in the neighborhood of C the respective projection value may be calculated and by using the transfer function TF(D) a color RGB value and an opacity A value can be derived. The pixels on the display at the positions where the surface positions are located in the neighborhood of the intersection point C are colored accordingly and optionally blended with a background image, which might be, for instance, a live fluoroscopy image and/or an image showing the pre-interventional three-dimensional representation of the vascular structure.

The transfer function can be a monochrome function or can provide a color mapping. In the case of a monochrome transfer function the projection values may be assigned to, for instance, different brightness and/or different degrees of opacity. For instance, a high brightness can be used to simulate a spotlight and a low brightness can be used to simulate a casted shadow as schematically and exemplarily illustrated in FIGS. 5 and 6. The projections in FIGS. 5 and 6 have been determined by using the Euclidean distance between the respective surface position PS and the position P of the tip and by using a monochromatic transfer function.

Figure 7:
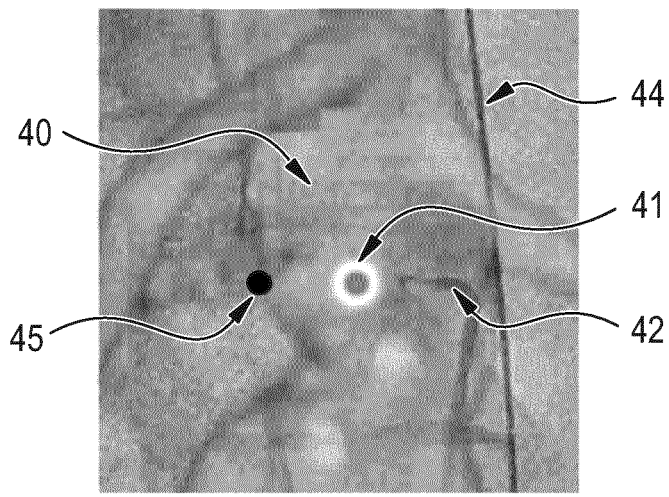
FIGS. 7 to 9 and 11 show further examples of projections of the tip of the catheter on a representation of a surface of the vascular structure overlaid on an x-ray fluoroscopy image.
Figure 8:
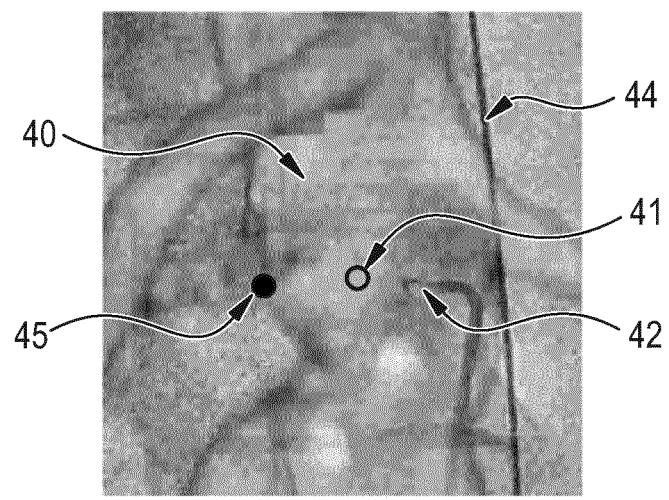
Figure 9:
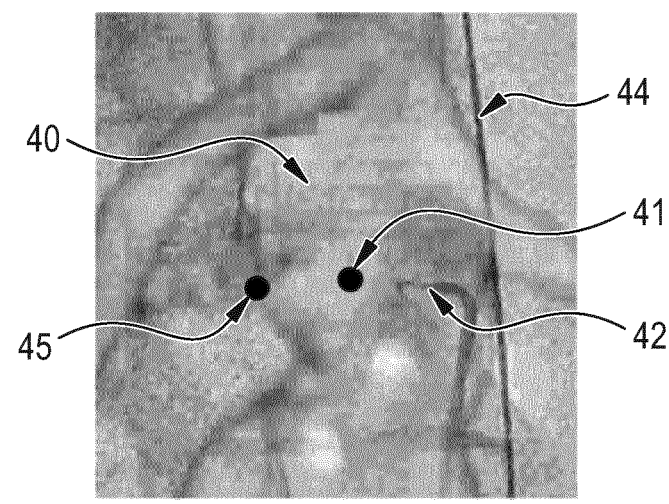

FIGS. 7 to 9 schematically and exemplarily illustrate different projections calculated by using different transfer functions. In FIG. 7 a projection 41 of the tip 42 of the catheter on the surface 40 of the vascular structure is shown, which has been determined by using a multi-color transfer function which assigns full opaque red color to surface points close to the center of the projection, i.e. close to the point of intersection of the line defined by the position and orientation of the tip 42 of the catheter and the surface 40 of the vascular structure. Moreover, the transfer function assigns slightly transparent yellow to surface points a bit further away from the center of the projection 41 and semitransparent green to surface points even further away. Surface points having an even larger distance are not colored. These different colored regions of the projection 41 can be defined by defining corresponding thresholds for thresholding the distance of the respective surface point to the center of the projection. For generating FIG. 8 another transfer function has been used. In this example the transfer function assigns opaque black to surface points projected at a predefined distance, i.e. having a predefined distance from the point of intersection, of, for example, 2 mm. In a further example shown in FIG. 9 the transfer function assigns opaque black to all surface points of the projection 41 at a distance being smaller than a predefined distance threshold like 2 mm from the center of the projection 41, i.e. from the intersection point.

In FIGS. 7 to 9 also the position at which the renal artery branches from the main artery is indicated, wherein for this indication a point 45 is used. Thus, the display 18 can also be adapted to indicate the position of a target to which the tip of the catheter should be moved. The target can be automatically or manually marked on the three-dimensional representation of the vascular structure 3 and then finally shown by the display 18. In FIGS. 7 to 9 the representation 40 of the vascular structure and the projection 41 are overlaid on a live fluoroscopy image generated by the fluoroscopy device 11 such that also a guidewire 44 used during the interventional procedure is shown in these figures.

Figure 10:
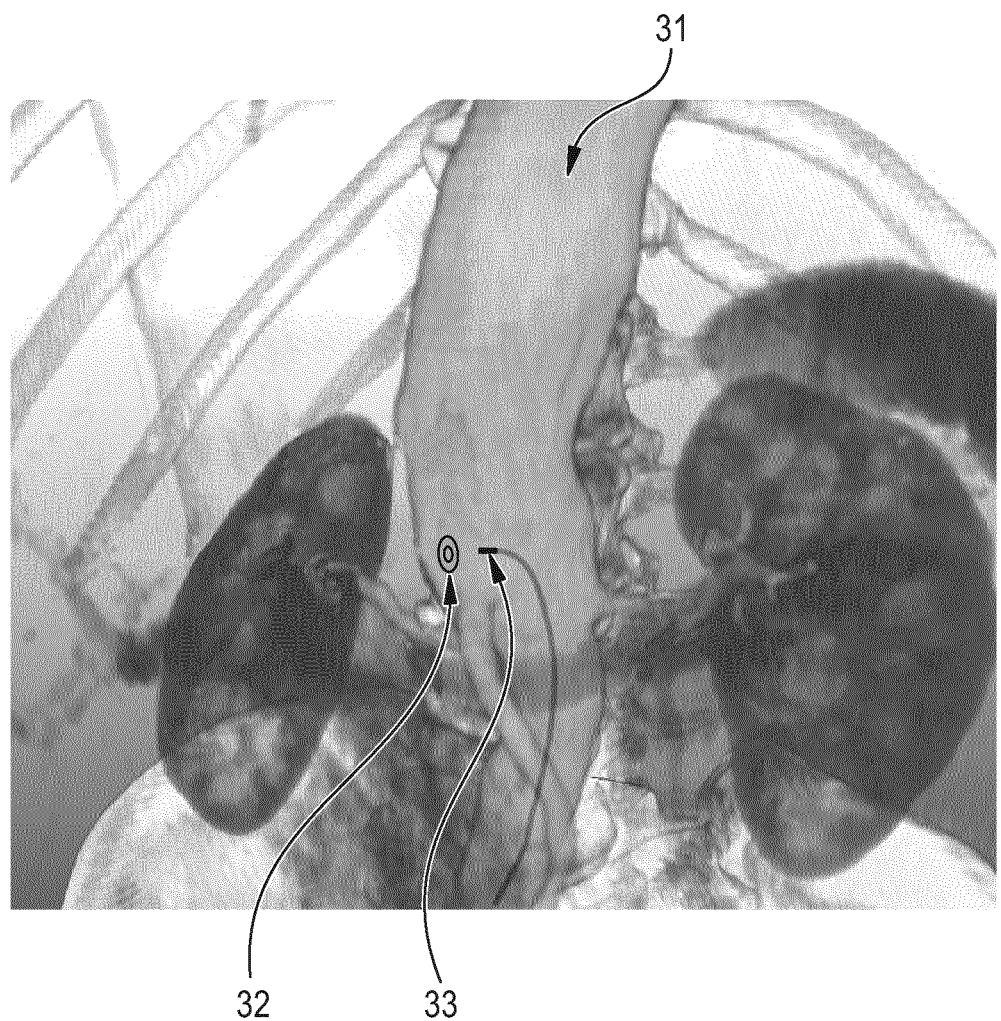
Figure 11:
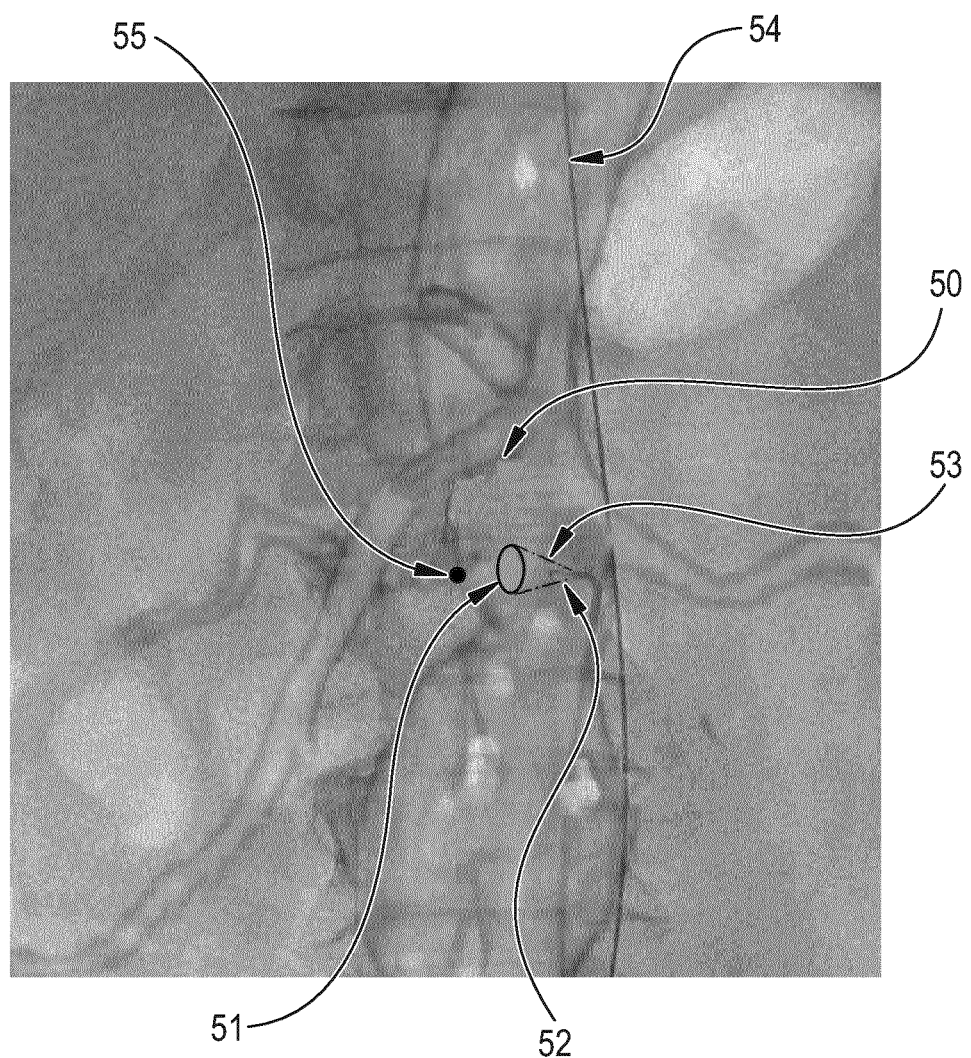

FIG. 10 shows schematically and exemplarily a further embodiment of a projection 32 of a tip 33 of a catheter on a surface of a vascular structure 31. In this example a transfer function has been used, which assigns opaque black to surface points at a first distance from the center of the projection 32 and to surface points at a second distance from the center of the projection 32, wherein these distances can be predefined and are optionally modifiable by the user. FIG. 11 schematically and exemplarily illustrates a further projection 51 on a surface of a vascular structure 50, wherein in this embodiment the transfer function assigns opaque black to surface points having a predefined distance to the center of the projection and the display is additionally adapted to indicate a cone 53 connecting the outer border of the projection 51 with the position of the tip 52 of the catheter. In FIG. 11 the representation 50 of the vascular structure and the projection 51 are overlaid on a live fluoroscopy image generated by the fluoroscopy device 11 such that also a guidewire 54 used during the interventional procedure is shown in FIG. 11. From FIG. 11 the user can obtain the information that the catheter needs to be twisted counter-clockwise, in order to reach the branch 55 to the renal artery.

Although in above described embodiments the first object is a tip of a catheter and the second object is a vascular structure within a person, in other embodiments the first and second objects can be other elements. For instance, the first object can be another medical device to be introduced into a person or a device to be introduced into a technical object. Moreover, the second object can be another part of the person like an organ of a living being like a heart, a kidney, et cetera. The second object can also be a technical object like a technical tubular system.

Although in above described embodiments certain techniques of determining a projection of the first object onto the representation of the surface of the second object have been described, in other embodiments also other techniques can be used for determining the projection. In particular, known ray casting techniques can be used for determining the projection of the first object onto the representation of the surface of the second object. In an embodiment a divergent radiation beam can be defined, which starts at the location of the distal tip of the catheter and which has a central ray being aligned with the longitudinal axis of the catheter, wherein the intersection of the divergent radiation beam with the surface of the second object can be calculated for determining the projection. Moreover, while determining the projection of the first object onto the representation of the surface of the second object, not only the orientation of a single axis of the first object like the orientation of the longitudinal axis 20 of the tip 10 of the catheter as described above with reference to FIG. 3 may be considered, but, for instance, also the orientations of one or two further axes like further transverse axes of the first object may be considered. In particular, the projection may be invariant with respect to a rotation of the first object around its longitudinal axis as described above with reference to FIG. 3, but in an embodiment the projection may also depend on a rotation of the first object around its longitudinal axis.

Although in above described embodiments a fluoroscopy device has been used, which generates x-ray projection images, in another embodiment the imaging apparatus may not use any x-rays, wherein the position of the first object relative to the second object can be determined by using a non-x-ray tracking technique like optical shape sensing or electromagnetic tracking, wherein the projection can be calculated based on this determined position of the first object and a representation of a surface of the second object and wherein finally the calculated projection can be shown on the representation of the surface optionally together with a representation of the first object at the tracked position of the first object.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of a projection of a first object on a surface of a representation of a second object, the provision of a representation of a target to which the first object should be moved within the second object, the provision of a three-dimensional representation of the second object, et cetera performed by one or several units or devices can also be performed by any other number of units or devices. These operations and/or the control of the imaging apparatus in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an imaging apparatus for imaging a first object like a tip of a catheter within a second object being, for instance, a vascular structure of a person. A three-dimensional representation of the second object including a representation of a surface of the second object and the position of the first object relative to the position of the second object are provided, and a projection of the first object onto the representation of the surface of the second object is determined and shown to a user like a physician on a display. The three-dimensional spatial relationship between the first object and the second object is thereby shown in a way that is very native for the user, i.e. a visualization can be provided, which allows the user to easily and accurately grasp the three-dimensional spatial relationship between the first object and the second object.

The invention claimed is:

1. An imaging apparatus for imaging a first object within a second object, the imaging apparatus comprising:
   a representation providing unit for providing a three-dimensional representation of the second object, wherein the three-dimensional representation includes a representation of a three-dimensional surface of the second object,
   a position providing unit for providing a position of the first object within the second object relative to a position of the second object,
   a projection unit for determining a surface position of a projection of the first object onto the representation of the three-dimensional surface of the second object based on the provided position of the first object, and
   a display for displaying the representation of the three-dimensional surface of the second object with the projection of the first object thereon:
   wherein the projection unit is adapted to:
   as the first object moves within the second object, calculate for different surface positions of the projections of the first object on the representation of the three-dimensional surface of the second object a projection value wherein the projection value depends on a distance between the respective surface position and the provided position of the first object,
   provide assignments between the projection values and visualization properties, and
   assign visualization properties to the surface positions based on the calculated projection values and the provided assignments, thereby determining the projection.

2. The imaging apparatus as defined in claim 1, wherein the position providing unit is adapted to also provide the orientation of the first object relative the second object, wherein the projection unit is adapted to calculate the projection of the first object onto the representation of the surface of the second object based on the provided position and orientation of the first object.

3. The imaging apparatus as defined in claim 2, wherein the projection unit is adapted to calculate the projection based on the point of intersection between the representation of the surface of the second object and a line defined by the position and orientation of the first object.

4. The imaging apparatus as defined in claim 3, wherein the projection unit is adapted to calculate the projection such that the point of intersection forms the center of the projection.

5. The imaging apparatus as defined in claim 1, wherein the projection unit is adapted to calculate a distance between the provided position of the first object and the respective surface position as the projection value.

6. The imaging apparatus as defined in claim 1, wherein the projection unit is adapted to:
   provide the orientation of the first object within the second object,
   calculate a point of intersection between the representation of the surface of the second object and a line defined by the position and orientation of the first object,
   calculate a distance between the point of intersection and the respective surface position as the projection value.

7. The imaging apparatus as defined in claim 6, wherein the projection unit is adapted to calculate the distance between the point of intersection and the respective surface position along the representation of the surface of the second object.

8. The imaging apparatus as defined in claim 1, wherein the projection unit is adapted to assign degrees of opacity and/or colors and/or brightness to the projection values as the visualization properties.

9. The imaging apparatus as defined in claim 1, wherein the display is further adapted to display a representation of the position of the first object relative to the representation of the surface of the second object.

10. The imaging apparatus as defined in claim 1, wherein the imaging apparatus further comprises an image providing unit for providing an image of the first object, wherein the display is adapted to display the projection of the first object on the representation of the surface overlaid with the provided image.

11. The imaging apparatus as defined in claim 1, wherein the second object comprises a wall having a front surface with respect to the viewing direction at one side of the wall and a back surface with respect to the viewing direction at another opposing side of the wall, wherein the projection unit is adapted to display the projection of the first object on the front and back surfaces with different visualization properties.

12. A system for moving a first object within a second object, wherein the system comprises:
a moving unit for moving the first object within the second object, and
an imaging apparatus as defined in claim 1 for imaging the first object within the second object.

13. A method of imaging a first object within a second object comprising:
providing a three-dimensional representation of the second object, wherein the three-dimensional representation includes a representation of a surface of the second object,
determining a position of the first object relative to a position of the second object as it moves within the second object,
determining a projection of the first object onto the representation of the surface of the second object based on the position of the first object relative to the second object, wherein the projection is a two-dimensional projection that depends on a spatial relationship between the first object and the second object,
calculating for different surface positions on the representation of the surface of the second object, projection values that depend on a distance between each of the surface positions and the position of the first object,
assigning visualization properties to the surface positions based on the calculated projection values, and
displaying the projection of the first object on the representation of the surface of the second object on a display with the assigned visualization properties corresponding to a current surface position.

14. A non-transitory computer-readable medium carrying a computer program configured to control one or more computer processors to perform the method as defined in claim 13.

15. An imaging apparatus for imaging a catheter within a tubular anatomical structure of a patient, the apparatus comprising:
a catheter positioning system configured to determine a position and orientation of a tip of the catheter, the catheter being movably disposed in the tubular anatomical structure;
a processor configured to:
receive a three-dimensional representation of at least one of an inner surface and an outer surface of the tubular anatomical structure,
determine a projection of the tip of the catheter and of a most distal point of the tip of the catheter onto one of the inner and outer surface of the tubular anatomical structure based on the determined position of the tip of the catheter,
as the catheter moves in the tubular anatomical structure, repeatedly calculating a value that depends on a distance between the one of the inner and outer surface of the tubular anatomical structure and the most distal point on the tip of the catheter,
assign at least one of color, brightness, opacity, or other visualization properties based on (a) at least one of the distance between the most distal point of the catheter and the one of the inner and outer surface of the tubular anatomical structure and (b) whether the distance is determined between the most distal point of the catheter and the inside surface or between the most distal point and the outside surface of the tubular anatomical structure;
a display device configured to be controlled by the processor to display at least one of the inside and outside surface of the tubular anatomical structure, the projection of the tip of the catheter, and the most distal point of the tip of the catheter with the projection of the tip of the catheter being displayed with at least one of the assigned color, brightness, opacity, or other visualization property.

* * * * *